(12) United States Patent
Haick et al.

(10) Patent No.: US 9,551,712 B2
(45) Date of Patent: Jan. 24, 2017

(54) VOLATILE ORGANIC COMPOUNDS AS DIAGNOSTIC MARKERS FOR VARIOUS TYPES OF CANCER

(75) Inventors: Hossam Haick, Haifa (IL); Meggie Hakim, Nazareth (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 13/520,193

(22) PCT Filed: Jan. 6, 2011

(86) PCT No.: PCT/IL2011/000017
§ 371 (c)(1),
(2), (4) Date: Jul. 2, 2012

(87) PCT Pub. No.: WO2011/083473
PCT Pub. Date: Jul. 14, 2011

(65) Prior Publication Data
US 2012/0326092 A1 Dec. 27, 2012

Related U.S. Application Data

(60) Provisional application No. 61/292,872, filed on Jan. 7, 2010.

(51) Int. Cl.
*G01N 33/497* (2006.01)
*H01J 49/26* (2006.01)
*G01N 30/00* (2006.01)
*G01N 33/574* (2006.01)

(52) U.S. Cl.
CPC .. *G01N 33/57419* (2013.01); *G01N 33/57415* (2013.01); *G01N 33/57434* (2013.01)

(58) Field of Classification Search
CPC ......... G01N 33/497; G01N 30/00; H01J 49/26
USPC ...... 436/64, 181, 813, 900; 73/23.3; 422/84; 252/408.1
See application file for complete search history.

(56) References Cited

U.S. PATENT DOCUMENTS

| | | | |
|---|---|---|---|
| 4,772,559 A | 9/1988 | Preti | |
| 5,693,715 A * | 12/1997 | Kodali | C08F 36/00 525/190 |
| 5,996,586 A * | 12/1999 | Phillips | 128/898 |
| 8,597,953 B2 * | 12/2013 | Haick | 436/64 |
| 2008/0220984 A1* | 9/2008 | Bright et al. | 506/12 |
| 2009/0239252 A1* | 9/2009 | Trevejo | C12Q 1/04 435/29 |
| 2011/0277538 A1* | 11/2011 | Haick | 73/23.3 |

FOREIGN PATENT DOCUMENTS

| | | |
|---|---|---|
| WO | 00/41623 | 7/2000 |
| WO | 03/014724 | 2/2003 |
| WO | 2004/008953 | 1/2004 |
| WO | 2006/112733 | 10/2006 |
| WO | 2008/151238 | 12/2008 |
| WO | 2009/004576 | 1/2009 |
| WO | 2009/144725 | 12/2009 |
| WO | WO 2009144725 A1 * | 12/2009 |
| WO | 2010/079490 | 7/2010 |
| WO | WO 2010079490 A1 * | 7/2010 |

OTHER PUBLICATIONS

Phillips et al., Prediction of Breast Cancer Using Volatile Biomarkers in the Breath, Breast Cancer Research and Treatment, 2006, 99, 19-21.*
Hazardous Substance Fact Sheet, 2-Methoxyethyl acetate, New Jersey Department of Health, 2009, 1-6.*
Hazardous Substance Fact Sheet, Cyclopentatriene, New Jersey Department of Health and Senior Services, 2002, 1-6.*
Peng et al., Diagnosing Lung Cancer in Exhaled Breath Using Gold Nanoparticles, Nature Nanotechnology, 2009, 4, 669-673.*
Livingston et al., Characterizing the Binder in Rock Paintings by THM-GC-MS: La Casa De Las Golondrinas, Guatemala, A Cautionary Tale for Radiocarbon Dating, International J. of Mass Spectrometry, 2009, 1-10.*
He et al., Gas Chromatographic-Mass Spectrometric Analysis for Volatile Organic Compound of Human Metabolites in Sealed Cabin, Fenxi Huaxue, 2001, 29(8), 978-982.*
Machado et al., Detection of Lung Cancer by Sensor Array Analysis of Exhaled Breath, Am J Crit Care Med, 2005, 171, 1286-1291.*
Peng et al., Detection of Lung, Breast, Colorectal, and Prostate Cancers From Exhaled Breath Using a Single Array of Nanosensors, British Journal of Cancer, 2010, 103, 542-551.*
Gomm, R., Chapter 3, Controlled Experiments, Social Research Methodology: A Critical Introduction, 2nd Addition, Palgrave MacMillan, 2008, 81.*
Phillips et al., Prediction of Breast Cancer Using Volatile Biomarkers in Breath, Breast Cancer Research and Treatment, 2006, 99, 19-21.*
Phillips et al., Variation in Volatile Organic Compounds in the Breath of Normal Humans, J. Chromatography B, 1999, 729, 75-88.* *Genetic Technologis Limited v. Merial L.L.C.*; Opinion of the United States Court of Appeals for the Federal Circuit, 2016, 1-20.*
*Ariosa Diagnostics, Inc. v. Sequenom, Inc.*; Opinion of the United States Court of Appeals for the Federal Circuit, 2015, 1-21.*
American Thoracic Society (ATS) and the European Respiratory Society (ERS)., ATS/ERS recommendations for standardized procedures for the online and offline measurement of exhaled lower respiratory nitric oxide and nasal nitric oxide, 2005. Am J Respir Crit Care Med 171(8):912-930.

(Continued)

*Primary Examiner* — Maria Leavitt
*Assistant Examiner* — Amy M Bunker
(74) *Attorney, Agent, or Firm* — Roach Brown McCarthy & Gruber, P.C.; Kevin D. McCarthy

(57) ABSTRACT

The present invention provides sets of VOCs for breath analysis. Methods of use thereof in diagnosing, monitoring or prognosing breast cancer, head and neck cancer, prostate cancer or colon cancer are disclosed.

7 Claims, 6 Drawing Sheets

(56) References Cited

OTHER PUBLICATIONS

Buszewski, Boguslaw et al., (2007) Human exhaled air analytics: biomarkers of diseases. Biomed Chromatogr 2(6):553-566.
Chen, Xing et al., (2005) A study of an electronic nose for detection of lung cancer based on a virtual SAW gas sensors array and imaging recognition method. Meas Sci Technol 16(8):1535-1546.
Chen, Xing et al., (2007) A study of the volatile organic compounds exhaled by lung cancer cells in vitro for breath diagnosis. Cancer 110(4):835-844.
Di Natale, Corrado et al. (2003) Lung cancer identification by the analysis of breath by means of an array of non-selective gas sensors. Biosens Bioelectron 18(10):1209-1218.
Filipiak, Wojciech et al., (2008) Release of volatile organic compounds (VOCs) from the lung cancer cell line CALU-1 in vitro. Cancer Cell Int 8:17.
Gaspar, Elvira M. et al., (2009) Organic metabolites in exhaled human breath—a multivariate approach for identification of biomarkers in lung disorders. J Chromatogr A 1216(14):2749-2756.
Gordon, S. M. et al., (1985) Volatile organic compounds in exhaled air from patients with lung cancer. Clin Chem 31(8):1278-1282.
Lindinger, W. et al., (1998) On-line monitoring of volatile organic compounds at pptv levels by means of proton-transfer-reaction mass spectrometry (PTR-MS) medical applications, food control and environmental research. Int. J Mass Spectrom Ion Process 173(3):191-241.
Lindinger, Werner et al., (2001) Environmental, food and medical applications of proton-transfer-reaction mass spectrometry (PTR-MS) Adv Gas Phase Ion Chem 4:1-35.
Miekisch, Wolfram et al., (2004) Diagnostic potential of breath analysis—focus on volatile organic compounds. Clin Chim Acta 347(1-2):25-39.
O'Neill, H. J. et al., (1988) A computerized classification technique for screening for the presence of breath biomarkers in lung cancer. Clin Chem 34(8):1613-1617.
Peng, Gang et al., (2009) Diagnosing lung cancer in exhaled breath using gold nanoparticles. Nat Nanotechnol 4(10):669-673.
Peng, G. et al., (2010) Detection of lung, breast, colorectal, and prostate cancers from exhaled breath using a single array of nanosensors. Br J Cancer 103(4):542-551.
Phillips, Michael et al., (1999) Volatile organic compounds in breath as markers of lung cancer: a cross-sectional study. Lancet 353(9168):1930-1933.
Phillips, Michael et al., (2003) Detection of lung cancer with volatile markers in the breath. Chest 123(6):2115-2123.
Phillips, Michael (2003) Volatile markers of breast cancer in the breath. Breast J 9(3):184-191.
Phillips, Michael et al., (2006) Prediction of breast cancer using volatile biomarkers in the breath. Breast Cancer Res Treat 99(1):19-21.
Phillips, M. et al., (2007) Prediction of lung cancer using volatile biomarkers in breath. Cancer Biomark 3(2):95-109.
Phillips, Michael et al., (2008) Detection of lung cancer using weighted digital analysis of breath biomarkers. Clin Chim Acta 393(2):76-84.
Poli, Diana et al., (2005) Exhaled volatile compounds in patients with non-small cell lung cancer: cross sectional and nested short-term follow-up study. Respiratory Research 6:71-81.
Poli, D. et al., (2008) Breath analysis in non small cell lung cancer patients after surgical tumour resection. Acta Biomed 79(Suppl 1):64-72.
Rock, Frank et al., (2008) Electronic nose: current status and future trends. Chem Rev 108(2):705-725.
Schmutzhard, Joachim et al., (2008) Pilot study: volatile organic compounds as a diagnostic marker for head and neck tumors. Head Neck 30(6):743-749.
Song, Geng et al., (2009) Quantitative breath analysis of volatile organic compounds of lung cancer patients. Lung Cancer 67(2):227-231.
Wehinger, Andreas et al., (2007) Lung cancer detection by proton transfer reaction mass-spectrometric analysis of human breath gas. Inter J Mass Spectrometry 265(1):49-59.
Witschi, Hanspeter et al., (1989) Metabolism and pulmonary toxicity of butylated hydroxytoluene (BHT). Pharmacol Ther. 42(1):89-113.
Yu, Hao et al., (2003) Detection volatile organic compounds in breath as markers of lung cancer using a novel electronic nose. Sensors, 2003. Proceedings of IEEE 2:1333-1337.
Zimmermann, Dunja et al., (2007) Determination of volatile products of human colon cell line metabolism by GC/MS analysis. Metabolomics 3(1):13-17.
ISR of PCTIL2011000017 Jun. 6, 2011.
Chan et al., (2009) Elevated levels of oxidative stress markers in exhaled breath condensate. Journal of Thoracic Oncology 4(2): 172-178.
Coggiola et al., (2004) Volatile organic biomarkers in exhaled breath as a rapid prodromal, diagnosis of bioagent infection. SRI International Menlo Park CA.

* cited by examiner

VOLATILE ORGANIC COMPOUNDS AS DIAGNOSTIC MARKERS FOR VARIOUS TYPES OF CANCER

REFERENCE TO CO-PENDING APPLICATIONS

Priority is claimed as a 371 of international application number PCT/IL2011/000017, filed on Jan. 6, 2011; which claims priority to U.S. Provisional Patent application Ser. No. 61/292,872, filed on Jan. 7, 2010.

FIELD OF THE INVENTION

The present invention relates to sets of volatile organic compounds indicative of various types of cancer, and methods of use thereof.

BACKGROUND OF THE INVENTION

Breath analysis has long been recognized as a reliable technique for diagnosing certain medical conditions including tissue inflammation (e.g. asthma), immune responses (e.g. to cancer cells or bacteria), metabolic disorders (e.g. diabetes), digestive processes, liver and/or kidney disorders, gum disease, halitosis, and other physiological conditions (Buszewski et al., Biomed. Chromatogr., 2007, 21, 553-566). The diagnosis is usually performed by collecting breath samples to a container followed by subsequent measurements of specific volatile organic compounds (VOCs).

The composition of VOCs in exhaled breath is dependent upon cellular metabolic processes. In control individuals, the composition provides a distinct chemical signature with relatively narrow variability between samples from a single individual and samples from different individuals. The composition of VOCs includes saturated and unsaturated hydrocarbons, oxygen containing compounds, sulfur containing compounds, nitrogen containing compounds, halogenated compounds, etc.

In exhaled breath of patients with cancer, different levels of certain VOCs including volatile $C_4$-$C_{20}$ alkane compounds, specific monomethylated alkanes as well as benzene derivatives were found. Hence, the composition of VOCs in exhaled breath of patients with cancer differs from that of control individuals, and can therefore be used to diagnose cancer, and to monitor disease progression or therapy-mediated disease regression. An additional advantage for diagnosing cancer through breath is the non-invasiveness of the technique which holds the potential for large-scale screening.

In recent years many attempts have been made to identify one specific pattern of volatile organic compounds (VOCs) in the breath of lung cancer patients. Phillips et al. (Lancet, 1999, 353, 1930-1933) used discriminant analysis to detect a combination of 22 breath VOCs as the "fingerprint" of lung cancer. Phillips et al. (Chest, 2003, 123, 2115-2123) then used a predictive model employing 9 VOCs that was found to exhibit sufficient sensitivity and specificity to be used as screen for lung cancer. In a more recent study, Phillips et al. (Cancer Biomarkers, 2007, 3, 95-109) described the use of multi-linear regression and fuzzy logic to analyze breath samples of lung cancer patients. This study provided a set of 16 VOCs as the major identifiers of primary lung cancer in breath. The use of weighted digital analysis to select 30 breath VOCs as candidate biomarkers of primary lung cancer was then employed (Phillips et al., Clinica Chimica Acta, 2008, 393, 76-84).

Yu et al. (Sensors, Proceedings of IEEE, 2003, 2, 1333-1337) used an electronic nose device with capillary column GC and a pair of surface acoustic wave sensors to detect 9 VOCs as markers for lung cancer. Chen et al. (Meas. Sci. Technol. 2005, 16, 1535-1546) used a set of 11 VOCs to calibrate sensors array based on surface acoustic wave to diagnose lung cancer patients. In another study, Chen et al. (Cancer, 2007, 110, 835-844) identified 4 special VOCs that were found to exist in all culture mediums of lung cancer cells and can be used as markers of lung cancer. Di Natale et al. (Biosensors and Bioelectronics, 2003, 18, 1209-1218) used an array of non-selective gas sensors for detecting various alkanes and benzene derivatives as possible candidate markers of lung cancer. Gordon et al. (Clin. Chem., 1985, 31(8), 1278-1282) used breath collection technique and computer-assisted gas chromatography/mass spectrometry (GC-MS) to identify several VOCs in the exhaled breath of lung cancer patients which appear to be associated with the disease. Song et al. (Lung Cancer, 2009, 67, 227-231) reported that 1-butanol and 3-hydroxy-2-butanone were found at significantly higher concentrations in the breath of the lung cancer patients compared to the controls. O'neill et al. (Clinical Chemistry, 1988, 34(8), 1613-1617) reported a list of 28 VOCs found in over 90% occurrence in expired-air samples from lung cancer patients. Wehinger et al. (Inter. J. Mass Spectrometry, 2007, 265, 49-59) used proton transfer reaction mass-spectrometric analysis to detect lung cancer in human breath. Two VOCs were found to best discriminate between exhaled breath of primary lung cancer cases and control. Gaspar et al. (J. Chromatography A, 2009, 1216, 2749-2756) used linear and branched $C_{14}$-$C_{24}$ hydrocarbons from exhaled air of lung cancer patients, smokers and non-smokers for multivariable analysis to identify biomarkers in lung disorders. Poli et al. (Respiratory Research, 2005, 6, 71-81) showed that the combination of 13 VOCs allowed the correct classification of cases into groups of smokers, patients with chronic obstructive pulmonary disease, patients with non-small cells lung cancer and controls. Recently, Poli et al. (Acta Biomed, 2008, 79(1), 64-72) measured VOC levels in exhaled breath of operated lung cancer patients, one month and three years after surgical removal of the tumor. Peng et al. (Nature Nanotech, 2009, 4, 669-673) identified 42 VOCs that represent lung cancer biomarkers using GC-MS.

In addition to the many studies that were aimed at identifying VOCs indicative of lung cancer from breath samples, Filipiak et al. (Cancer Cell International, 2008, 8, 17) disclosed a list of 60 substances observed in the headspace of medium as well as in the headspace of lung cancer cell line CALU-1. A significant increase in the concentrations of 4 VOCs and a decrease in the concentrations of 11 VOCs as compared to medium controls were detected after 18 hours.

These studies, however, cumulatively provided over 150 VOCs as potential lung cancer biomarkers in breath samples, thus failing to determine a single set of VOCs to be used as a diagnostic tool for lung cancer screening.

Although many of the ongoing efforts were aimed at identifying a unique set of VOCs in the breath of lung cancer patients, several studies were directed to identifying other cancer types through breath. Phillips et al. (The Breast Journal, 2003, 9(3), 184-191) used 8 breath VOCs to identify women with breast cancer. In another study, Phillips et al. (Breast Cancer Research and Treatment, 2006, 99, 19-21) identified 5 VOCs as breath biomarkers of breast cancer that predicted breast cancer in the prediction set with 93% sensitivity and 84.6% specificity. Zimmermann et al. (Metabolomics, 2007, 3(1), 13-17) detected 4 VOC metabolites in colon cancer cell lines. These metabolites were not detected in normal colon cell line. Schmutzhard et al. (Head & Neck, 2008, 30(6), 743-749) used a proton transfer reaction-mass spectrometry to measure 42 different masses from patients with head and neck tumors which showed a statistically significant difference compared to control groups. The masses were not assigned to particular VOCs.

WO 2000/041623 to Phillips discloses a process for determining the presence or absence of a disease, particularly breast or lung cancer, in a mammal, comprising collecting a representative sample of alveolar breath and a representative sample of ambient air, analyzing the samples of breath and air to determine content of n-alkanes having 2 to 20 carbon atoms, inclusive, calculating the alveolar gradients of the n-alkanes in the breath sample in order to determine the alkane profile, and comparing the alkane profile to baseline alkane profiles calculated for mammals known to be free of the disease to be determined, wherein finding of differences in the alkane profile from the baseline alkane profile being indicative of the presence of the disease.

WO 2010/079491 to Haick discloses a set of volatile organic compounds comprising at least butylated hydroxytoluene or 4,6-di(1,1-dimethylethyl)-2-methyl-phenol for breath analysis. Methods of use thereof in diagnosing, monitoring or prognosing lung cancer are also disclosed.

There is an unmet need for sets of VOCs as diagnostic markers for various cancer types. Furthermore, there is an unmet need for the identification of unique signatures of various cancers in breath samples to enable non-invasive large scale screening.

SUMMARY OF THE INVENTION

The present invention provides methods of diagnosis, prognosis and monitoring of various types of cancer by determining the levels of signature sets of volatile organic compounds (VOCs) in a breath sample, wherein significantly different levels of said VOCs compared to a control sample are indicative for the presence of either one of breast, head and neck, prostate and colon cancers. Methods of identifying sets of volatile organic compounds indicative of the various types of cancer are further disclosed.

The present invention is based in part on the unexpected finding that breath samples that were obtained from cancer patients are characterized by unique sets of VOCs that were not previously recognized as being indicative of either one of breast, head and neck, prostate and colon cancers. These VOCs are present in significantly different levels in breath samples of patients having cancer as compared to control individuals. Thus, it is now disclosed for the first time that the presence of these signature sets of VOCs in levels which significantly differ from predetermined values provide improved sensitivity and specificity in diagnosing cancer through breath.

According to a first aspect, the present invention provides a method of identifying a set of VOCs indicative of cancer selected from the group consisting of breast cancer, colon cancer, head and neck cancer and prostate cancer, comprising the steps of:
  a) collecting a breath sample from a cancer patient;
  b) determining the levels of VOCs in said sample;
  c) comparing the levels of VOCs in the breath sample from the cancer patient to the levels of VOCs in a control sample; and
  d) identifying a set of VOCs having levels that are significantly different in the breath sample from the cancer patient as compared with the control sample thereby identifying a set of VOCs indicative of cancer selected from the group consisting of breast cancer, colon cancer, head and neck cancer and prostate cancer,
wherein the set of VOCs indicative of breast cancer comprises at least one of 2-amino-5-isopropyl-8-methyl-1-azulenecarbonitrile, 6-ethyl-3-octyl ester-2-trifluoromethylbenzoic acid, 2,3,4,6-tetramethoxystyrene, 2,4,6-tris(1-methylethyl)-phenol, 1,3,5-cycloheptatriene, and 2-methoxy-acetate ethanol; or
wherein the set of VOCs indicative of colon cancer comprises 1,3,5-cycloheptatriene; or
wherein the set of VOCs indicative of head and neck cancer comprises at least one of butylated hydroxytoluene, 1-methyl-3-(1-methylethyl)-benzene, and 4,6-di(1,1-dimethylethyl)-2-methyl-phenol; or
wherein the set of VOCs indicative of prostate cancer comprises at least one of 2-amino-5-isopropyl-8-methyl-1-azulenecarbonitrile, 2,2-dimethyl-decane, carbonic dihydrazide, 4,6-di(1,1-dimethylethyl)-2-methyl-phenol, and butylated hydroxytoluene. Each possibility represents a separate embodiment of the invention.

According to one aspect, the present invention provides a method of identifying a set of volatile organic compounds indicative of breast cancer comprising the steps of:
  a) collecting a breath sample from a breast cancer patient;
  b) determining the levels of volatile organic compounds in said sample;
  c) comparing the levels of volatile organic compounds in the breath sample from the breast cancer patient to the levels of volatile organic compounds in a control sample; and
  d) identifying a set of volatile organic compounds having levels that are significantly different in the breath sample from the breast cancer patient as compared with the control sample thereby identifying a set of volatile organic compounds indicative of breast cancer,
wherein the set of volatile organic compounds comprises at least one of 2-amino-5-isopropyl-8-methyl-1-azulenecarbonitrile, 6-ethyl-3-octyl ester-2-trifluoromethylbenzoic acid, 2,3,4,6-tetramethoxystyrene, 2,4,6-tris(1-methyl ethyl)-phenol, 1,3,5-cycloheptatriene, and 2-methoxy-acetate ethanol. Each possibility represents a separate embodiment of the invention.

In one embodiment, the set of volatile organic compounds indicative of breast cancer comprises at least one volatile organic compound. According to another embodiment, the set comprises at least 3 volatile organic compounds. According to yet another embodiment, the set comprises at least 5 volatile organic compounds. According to further embodiments, the set comprises at least 7 volatile organic compounds.

According to another aspect, the present invention provides a method of diagnosing, monitoring, and prognosing breast cancer in a subject comprising the steps of:
  a) collecting a breath sample from a subject;
  b) determining the level of at least one volatile organic compound from a set of volatile organic compounds in the sample, wherein the set of volatile organic compounds comprises at least one of 2-amino-5-isopropyl-8-methyl-1-azulenecarbonitrile, 6-ethyl-3-octyl ester-2-trifluoromethylbenzoic acid, 2,3,4,6-tetramethoxystyrene, 2,4,6-tris(1-methylethyl)-phenol, 1,3,5-cycloheptatriene, and 2-methoxy-acetate ethanol; and c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of breast cancer.

In particular embodiments, the set of volatile organic compounds indicative of breast cancer comprises at least one additional volatile organic compound, wherein the at least one additional volatile organic compound is 2-methyl-1,3-butadiene.

In other embodiments, the set of volatile organic compounds indicative of breast cancer further comprises at least one additional volatile organic compound selected from the group consisting of 3,3-dimethyl-pentane, 5-(2-methylpropyl)-nonane, 2,3,4-trimethyl-decane, 2,2,4,4,6,8,8-heptamethyl-nonane, ethyl benzene, 2,2,4,4,5,5,7,7-octamethyloctane, hydroxymethyl 2-hydroxy-2-methylpropionate, and 2-methyl-hexane. Each possibility represents a separate embodiment of the invention.

According to yet another aspect, the present invention provides a method of identifying a set of volatile organic compounds indicative of head and neck cancer comprising the steps of:
  a) collecting a breath sample from a head and neck cancer patient;
  b) determining the levels of volatile organic compounds in said sample;
  c) comparing the levels of volatile organic compounds in the breath sample from the head and neck cancer patient to the levels of volatile organic compounds in a control sample; and
  d) identifying a set of volatile organic compounds having levels that are significantly different in the breath sample from the head and neck cancer patient as compared with the control sample thereby identifying a set of volatile organic compounds indicative of head and neck cancer,
  wherein the set of volatile organic compounds comprises at least one of butylated hydroxytoluene, 1-methyl-3-(1-methylethyl)-benzene, and 4,6-di(1,1-dimethylethyl)-2-methyl-phenol. Each possibility represents a separate embodiment of the invention.

In various embodiments, the set of volatile organic compounds indicative of head and neck cancer comprises at least one volatile organic compound. According to another embodiment, the set comprises at least 3 volatile organic compounds. According to yet another embodiment, the set comprises at least 5 volatile organic compounds. According to further embodiments, the set comprises at least 7 volatile organic compounds.

According to yet another aspect, the present invention provides a method of diagnosing, monitoring, and prognosing head and neck cancer in a subject comprising the steps of:
  a) collecting a breath sample from a subject;
  b) determining the level of at least one volatile organic compound from a set of volatile organic compounds in the sample, wherein the set of volatile organic compounds comprises at least one of butylated hydroxytoluene, 1-methyl-3-(1-methylethyl)-benzene, and 4,6-di(1,1-dimethylethyl)-2-methyl-phenol; and
  c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of head and neck cancer.

In particular embodiments, the set of volatile organic compounds indicative of head and neck cancer comprises at least one additional volatile organic compound selected from the group consisting of 2-methyl-1,3-butadiene and 1,3-pentadiene. Each possibility represents a separate embodiment of the invention.

In other embodiments, the set of volatile organic compounds indicative of head and neck cancer further comprises at least one additional volatile organic compound selected from the group consisting of 2-acetylmethylamino-4,5,6,7-tetrahydrobenzothiazol-7-one, 2,2,4,4,6,8,8-heptamethyl-nonane, 4-(4-propylcyclohexyl)-4'-cyano[1,1'-biphenyl]-4-yl ester benzoic acid, carbonic dihydrazide, 2,2,3-trimethyl-bicyclo[2.2.1]heptane, and 1-propanol. Each possibility represents a separate embodiment of the invention.

According to an additional aspect, the present invention provides a method of identifying a set of volatile organic compounds indicative of prostate cancer comprising the steps of:
  a) collecting a breath sample from a prostate cancer patient;
  b) determining the levels of volatile organic compounds in said sample;
  c) comparing the levels of volatile organic compounds in the breath sample from the prostate cancer patient to the levels of volatile organic compounds in a control sample; and
  d) identifying a set of volatile organic compounds having levels that are significantly different in the breath sample from the prostate cancer patient as compared with the control sample thereby identifying a set of volatile organic compounds indicative of prostate cancer,
  wherein the set of volatile organic compounds comprises at least one of 2-amino-5-isopropyl-8-methyl-1-azulenecarbonitrile, 2,2-dimethyl-decane, carbonic dihydrazide, 4,6-di(1,1-dimethylethyl)-2-methyl-phenol, and butylated hydroxytoluene. Each possibility represents a separate embodiment of the invention.

In various embodiments, the set of volatile organic compounds indicative of prostate cancer comprises at least one volatile organic compound. According to another embodiment, the set comprises at least 3 volatile organic compounds. According to yet another embodiment, the set comprises at least 5 volatile organic compounds. According to further embodiments, the set comprises at least 7 volatile organic compounds.

According to a further aspect, the present invention provides a method of diagnosing, monitoring, and prognosing prostate cancer in a subject comprising the steps of:
  a) collecting a breath sample from a subject;
  b) determining the level of at least one volatile organic compound from a set of volatile organic compounds in the sample, wherein the set of volatile organic compounds comprises at least one of 2-amino-5-isopropyl-8-methyl-1-azulenecarbonitrile, 2,2-dimethyl-decane, carbonic dihydrazide, 4,6-di(1,1-dimethylethyl)-2-methyl-phenol, and butylated hydroxytoluene; and
  c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of prostate cancer.

In particular embodiments, the set of volatile organic compounds indicative of prostate cancer comprises at least one additional volatile organic compound selected from the group consisting of 2-methyl-1,3-butadiene and p-xylene. Each possibility represents a separate embodiment of the invention.

In other embodiments, the set of volatile organic compounds indicative of prostate cancer further comprises at least one additional volatile organic compound selected from the group consisting of toluene, 2,2,4,4,5,5,7,7-octamethyloctane, 1,1'-(1,3,3-trimethyl-1-propene-1,3-diyl)bis-benzene, α-phellandrene, dimethyl-diazene, and 1-ethyl-3,5-dimethyl-benzene. Each possibility represents a separate embodiment of the invention.

According to another aspect, the present invention provides a method of identifying a set of volatile organic compounds indicative of colon cancer comprising the steps of:
 a) collecting a breath sample from a colon cancer patient;
 b) determining the levels of volatile organic compounds in said sample;
 c) comparing the levels of volatile organic compounds in the breath sample from the colon cancer patient to the levels of volatile organic compounds in a control sample; and
 d) identifying a set of volatile organic compounds having levels that are significantly different in the breath sample from the colon cancer patient as compared with the control sample thereby identifying a set of volatile organic compounds indicative of colon cancer, wherein the set of volatile organic compounds comprises 1,3,5-cycloheptatriene.

In various embodiments, the set of volatile organic compounds indicative of colon cancer comprises at least 3 volatile organic compounds. According to yet another embodiment, the set comprises at least 5 volatile organic compounds. According to further embodiments, the set comprises at least 7 volatile organic compounds.

According to yet another aspect, the present invention provides a method of diagnosing, monitoring, and prognosing colon cancer in a subject comprising the steps of:
 a) collecting a breath sample from a subject;
 b) determining the level of at least one volatile organic compound from a set of volatile organic compounds in the sample, wherein the set of volatile organic compounds comprises 1,3,5-cycloheptatriene; and
 c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of colon cancer.

In particular embodiments, the set of volatile organic compounds indicative of colon cancer comprises at least one additional volatile organic, wherein the at least one additional volatile organic compound is 2-methyl-1,3-butadiene. In other embodiments, the at least one additional volatile organic compound is dimethyl-diazene.

In other embodiments, the set of volatile organic compounds indicative of colon cancer further comprises at least one additional volatile organic compound selected from the group consisting of 1,3-dimethyl benzene, 4-(4-propylcyclohexyl)-4'-cyano[1,1'-biphenyl]-4-yl ester benzoic acid, 1-methyl-3-(1-methylethyl)-benzene, 1,1'-(1-butenylidene) bis-benzene, 1-iodo-nonane, [(1,1-dimethylethyl)thio]-acetic acid, 2-amino-5-isopropyl-8-methyl-1-azulenecarbonitrile, 3,3-dimethyl-hexane, 1-ethyl-2,4-dimethyl-benzene, 2,4,6-tris(1-methylethyl)-phenol, 1,1'-(3-methyl-1-propene-1,3-diyl)bis-benzene, 2,6-bis(1,1-dimethylethyl)-4-methyl-methylcarbamate phenol, trans-1,4-diethylcyclohexane, ammonium acetate, and 2,2,3-trimethyl-endo-bicyclo[2.2.1]heptane. Each possibility represents a separate embodiment of the invention.

In certain embodiments, the level of the at least one volatile organic compound in the sample is significantly increased as compared to the level of said compound in a control sample. According to other embodiments, the level of the at least one volatile organic compound in the sample is significantly decreased as compared to the level of said compound in a control sample.

In particular embodiments, the levels of a plurality of volatile organic compounds in the breath sample from the cancer patient form a pattern which is significantly different from the pattern of said volatile organic compounds in the control sample. According to further embodiments, the pattern is significantly different from a predetermined pattern of occurrence of volatile organic compounds in breath samples.

The pattern can be analyzed with a pattern recognition analyzer which utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention.

In an exemplary embodiment, the algorithm used to analyze the pattern is principal component analysis.

According to various embodiments, the control sample may be obtained from a reference group comprising subjects which are not afflicted with cancer (negative control). The control sample, according to the principles of the present invention is obtained from at least one subject, preferably a plurality of subjects. A set of control samples from subjects who are not afflicted with cancer may be stored as a reference collection of data.

In certain embodiments, the test subject is a mammal, preferably a human.

In specific embodiments, the test subject is selected from a subject who is at risk of developing cancer, a subject who is suspected of having cancer, and a subject who is afflicted with cancer. Each possibility represents a separate embodiment of the invention.

According to some embodiments, the step of determining the levels of volatile organic compounds in a sample comprises the use of at least one technique selected from the group consisting of Gas-Chromatography (GC), GC-lined Mass-Spectrometry (GC-MS), Proton Transfer Reaction Mass-Spectrometry (PTR-MS), Electronic nose device, and Quartz Crystal Microbalance (QCM). Each possibility represents a separate embodiment of the invention.

In a particular embodiment, the step of determining the levels of volatile organic compounds in a sample further comprises the use of at least one of a breath concentrator and a dehumidifying unit.

In an exemplary embodiment, the step of determining the levels of volatile organic compounds in a sample comprises the use of Gas-Chromatography-Mass Spectrometry (GC-MS) combined with solid phase microextraction (SPME).

In specific embodiments, solid phase microextraction comprises the use of extraction fibers coated with at least one polymer selected from the group consisting of polydimethylsiloxane, polydimethylsiloxane-divinylbenzene and polydimethylsiloxane-carboxen. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
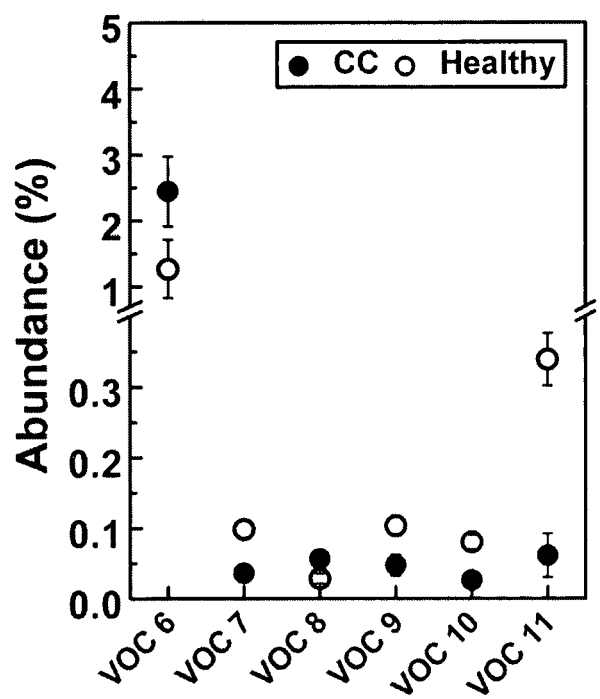
FIG. 1A. The abundance of 6 VOCs detected in breath samples of colon cancer patients (CC) and control individuals (healthy). VOC 6=1,1'-(1-butenylidene)bis benzene (m/z=208); VOC 7=1,3-dimethyl benzene (m/z=91); VOC 8=1-iodo nonane (m/z=43); VOC 9=[(1,1-dimethylethyl)thio]acetic acid (m/z=57); VOC 10=4-(4-propylcyclohexyl)-4'-cyano[1,1'-biphenyl]-4-yl ester benzoic acid (m/z=257); and VOC 11=2-amino-5-isopropyl-8-methyl-1-azulenecarbonitrile (m/z=224).

The present invention provides signature sets of volatile organic compounds as breath biomarkers for various types of cancer. Methods of analyzing the signature set for diagnosing cancer selected from breast, head and neck, prostate and colon cancers are disclosed.

The sets of the VOCs described in the present invention comprise unique breath volatile organic compounds and unique combinations thereof. Nowhere in the background art was it taught or suggested that the occurrence of these compounds and combinations thereof in certain levels in the breath of an individual can be used to diagnose cancer selected from breast, head and neck, prostate and colon cancer. The present invention provides methods of breath analysis wherein sets of volatiles enable improved sensitivity and specificity for determining the presence of cancer.

The present invention provides a set of volatile organic compounds indicative of breast cancer in a breath sample, wherein the set comprises at least one volatile organic compound. According to some embodiments, the at least one volatile organic compound is selected from 2-amino-5-isopropyl-8-methyl-1-azulenecarbonitrile, 6-ethyl-3-octyl ester-2-trifluoromethylbenzoic acid, 2,3,4,6-tetramethoxystyrene, 2,4,6-tris(1-methylethyl)-phenol, 1,3,5-cycloheptatriene, and 2-methoxy-acetate ethanol. Each possibility represents a separate embodiment of the invention. In specific embodiments, the set comprises between 1 and 3 VOCs. Alternatively, the set comprises between 1 and 5 VOCs. In another alternative, the set comprises between 1 and 7 VOCs. The set of volatile organic compounds used as biomarkers for breast cancer may further include 2-methyl-1,3-butadiene.

The signature set of VOCs indicative of breast cancer may further include at least one additional VOC selected from 3,3-dimethyl-pentane, 5-(2-methylpropyl)-nonane, 2,3,4-trimethyl-decane, 2,2,4,4,6,8,8-heptamethyl-nonane, ethyl benzene, 2,2,4,4,5,5,7,7-octamethyloctane, hydroxymethyl 2-hydroxy-2-methylpropionate, and 2-methyl-hexane. Each possibility represents a separate embodiment of the invention.

The present invention further provides a set of volatile organic compounds indicative of head and neck cancer in a breath sample, wherein the set comprises at least one volatile organic compound. According to some embodiments, the at least one volatile organic compound is selected from butylated hydroxytoluene, 1-methyl-3-(1-methylethyl)-benzene, and 4,6-di(1,1-dimethylethyl)-2-methyl-phenol. Each possibility represents a separate embodiment of the invention. In specific embodiments, the set comprises between 1 and 3 VOCs. Alternatively, the set comprises between 1 and 5 VOCs. In another alternative, the set comprises between 1 and 7 VOCs. The set of volatile organic compounds used as biomarkers for head and neck cancer may further include at least one of 2-methyl-1,3-butadiene and 1,3-pentadiene. Each possibility represents a separate embodiment of the invention.

The signature set of VOCs indicative of head and neck cancer may further include at least one additional VOC selected from 2-acetylmethylamino-4,5,6,7-tetrahydrobenzothiazol-7-one, 2,2,4,4,6,8,8-heptamethyl-nonane, 4-(4-propylcyclohexyl)-4'-cyano[1,1'-biphenyl]-4-yl ester benzoic acid, carbonic dihydrazide, 2,2,3-trimethyl-bicyclo[2.2.1]heptane, and 1-propanol. Each possibility represents a separate embodiment of the invention.

The present invention further provides a set of volatile organic compounds indicative of prostate cancer in a breath sample, wherein the set comprises at least one volatile organic compound. According to some embodiments, the at least one volatile organic compound is selected from 2-amino-5-isopropyl-8-methyl-1-azulenecarbonitrile, 2,2-dimethyl-decane, carbonic dihydrazide, 4,6-di(1,1-dimethylethyl)-2-methyl-phenol, and butylated hydroxytoluene. Each possibility represents a separate embodiment of the invention. In specific embodiments, the set comprises between 1 and 3 VOCs. Alternatively, the set comprises between 1 and 5 VOCs. In another alternative, the set comprises between 1 and 7 VOCs. The set of volatile organic compounds used as biomarkers for prostate cancer may further include at least one of 2-methyl-1,3-butadiene and p-xylene. Each possibility represents a separate embodiment of the invention.

The signature set of VOCs indicative of prostate cancer may further include at least one additional VOC selected from toluene, 2,2,4,4,5,5,7,7-octamethyloctane, 1,1'-(1,3,3-trimethyl-1-propene-1,3-diyl)bis-benzene, α-phellandrene, dimethyl-diazene, and 1-ethyl-3,5-dimethyl-benzene. Each possibility represents a separate embodiment of the invention.

The present invention further provides a set of volatile organic compounds indicative of colon cancer in a breath sample, wherein the set comprises at least one volatile organic compound. According to some embodiments, the at least one volatile organic compound is 1,3,5-cycloheptatriene. In specific embodiments, the set comprises between 1 and 3 VOCs. Alternatively, the set comprises between 1 and 5 VOCs. In another alternative, the set comprises between 1 and 7 VOCs. The volatile organic compounds used as biomarkers for colon cancer may further include at least one of 2-methyl-1,3-butadiene and dimethyl-diazene. Each possibility represents a separate embodiment of the invention.

The signature set of VOCs indicative of colon cancer may further include at least one additional VOC selected from 1,3-dimethyl benzene, 4-(4-propylcyclohexyl)-4'-cyano[1,1'-biphenyl]-4-yl ester benzoic acid, 1-methyl-3-(1-methylethyl)-benzene, 1,1'-(1-butenylidene)bis-benzene, 1-iodo-nonane, [(1,1-dimethylethyl)thio]acetic acid, 2-amino-5-isopropyl-8-methyl-1-azulenecarbonitrile, 3,3-dimethyl-hexane, 1-ethyl-2,4-dimethyl-benzene, 2,4,6-tris(1-methylethyl)-phenol, 1,1'-(3-methyl-1-propene-1,3-diyl)bis-benzene, 2,6-bis(1,1-dimethylethyl)-4-methyl-methylcarbamate phenol, trans-1,4-diethylcyclohexane, ammonium acetate, and 2,2,3-trimethyl-endo-bicyclo[2.2.1]heptane. Each possibility represents a separate embodiment of the invention.

A set of VOCs is determined by the distributions of VOCs in breath samples from cancer patients in comparison to the distributions of the same VOCs in control breath samples. The control breath samples, according to the principles of the present invention are obtained from a control individual, i.e., an individual not having cancer or any other chronic disease. The set of VOCs comprises specific VOCs for which a statistically significant difference in their level in samples from cancer patients as compared to samples from control subjects exists. The term "significantly different" as used herein refers to a quantitative difference in the concentration or level of each VOC from the set or combinations of VOCs as compared to the levels of VOCs in control samples obtained from individuals not having cancer. A statistically significant difference can be determined by any test known to the person skilled in the art. Common tests for statistical significance include, among others, t-test, ANOVA1 Kruskal-Wallis, Wilcoxon, Mann-Whitney and odds ration. Individual samples (of unknown status) can be compared with data from the reference group (negative control). An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. Statistical significance may alternatively be calculated as $P<0.05$. Methods of determining statistical significance are known and are readily used by a person of skill in the art. In a further alternative, increased levels, decreased levels, deviation, and changes can be determined by recourse to assay reference limits or reference intervals. These can be calculated from intuitive assessment or non-parametric methods. Overall, these methods calculate the 0.025, and 0.975 fractiles as $0.025*(n+1)$ and $0.975*(n+1)$. Such methods are well known in the art. The presence of a VOC marker which is absent in a control sample, is also contemplated as an increased level, deviation or change. The absence of a VOC marker which is present in a control, for example, is also contemplated as a decreased level, deviation or change. In some embodiments, individual samples (of unknown status) can be compared with data obtained from a positive control group known to have cancer. In accordance with these embodiments, a significantly different level of at least one VOC in the test sample as compared to the level of said compound in the control sample would be diagnosed as is known in the art.

According to the principles of the present invention, the set of volatile organic compounds which is indicative of a particular cancer type comprises VOCs that are present in breath samples of cancer patients of a particular cancer type in levels which are at least one standard deviation [SD] larger or smaller than their mean level in breath samples of a negative control population. More preferably, the levels of VOCs in breath samples of cancer patients of a particular cancer type are at least 2[SD] or 3[SD] larger or smaller than their mean level in breath samples of a negative control population. Accordingly, individual samples (of unknown status) are considered to belong to a sick population when the level of VOCs is at least 1[SD], 2[SD] or 3[SD] larger or smaller than the mean level of VOCs in breath samples of a negative control population.

Alternatively, the set of VOCs is characterized by a pattern which significantly differs from the patterns of said VOCs in control samples, or wherein the pattern is significantly different from a predetermined pattern of occurrence of VOCs.

The difference in the pattern can be analyzed with a pattern recognition analyzer which utilizes various algorithms including, but not limited to, principal component analysis, Fischer linear analysis, neural network algorithms, genetic algorithms, fuzzy logic pattern recognition, and the like. Exemplary algorithms are artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention.

Many of the algorithms are neural network based algorithms. A neural network has an input layer, processing layers and an output layer. The information in a neural network is distributed throughout the processing layers which are composed of nodes that simulate the neurons which are interconnected to the nodes. The analysis is performed by a series of vector matrix multiplications. Similar to statistical analysis which reveals underlying patterns in a collection of data, neural networks locate consistent patterns in a collection of data, based on predetermined criteria.

An exemplary pattern recognition algorithm is principal component analysis. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

The present invention thus provides a method of identifying sets of volatile organic compounds by determining the levels of VOCs in breath samples obtained from either one of breast, head and neck, prostate or colon cancer patients and comparing them to the levels of VOCs in a negative control sample, wherein significantly differing levels of volatile organic compound in samples from cancer patients as compared to the levels of said compounds in a negative control sample allow the determination of VOCs which are indicative of either one of breast, head and neck, prostate or colon cancer.

The present invention further provides a method of diagnosing, monitoring or prognosing cancer selected from breast cancer, head and neck cancer, prostate cancer and colon cancer in a subject. The method comprises the collection of a breath sample from a test subject followed by the determination of the level of at least one VOC from a set of VOCs which are indicative of a particular cancer type. The method then comprises comparing the level of said VOC with the levels of said VOC in a control sample, wherein significantly differing levels of said VOC in the test sample as compared to the levels of said VOC in the control sample is indicative of either one of breast, head and neck, prostate or colon cancer.

The collection of a breath sample, according to the principles of the present invention, can be performed in any manner known to a person of ordinary skill in the art. In exemplary embodiments, the breath sample may be collected using a breath collector apparatus. Specifically, the breath collector apparatus is designed to collect alveolar breath samples. Exemplary breath collector apparatuses within the scope of the present invention include apparatuses approved by the American Thoracic Society/European Respiratory Society (ATS/ERS); Silkoff et al., Am. J. Respir. Crit. Care Med., 2005, 171, 912). Alveolar breath is usually collected from individuals using the off-line method.

In certain embodiments, the sample is pre-concentrated prior to the measurement of VOCs. Breath concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). Non-limiting examples of coating polymers include polydimethylsiloxane, polydimethylsiloxane-divinylbenzene and polydimethylsiloxane-carboxen.

II. Sorbent Tubes—Sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Compounds are trapped onto the sorbent material throughout the sampling period. This technique was developed by the US National Institute for Occupational Safety and Health (NIOSH).

III. Cryogenic Concentrations—Cryogenic condensation is a process that allows recovery of volatile organic compounds (VOCs) for reuse. The condensation process requires very low temperatures so that VOCs can be condensed. Traditionally, chlorofluorocarbon (CFC) refrigerants have been used to condense the VOCs. Currently, liquid nitrogen is used in the cryogenic (less than −160° C.) condensation process.

Provided herein is the use of sets of VOCs from breath samples for the diagnosis, prognosis and/or monitoring of cancer, monitoring disease progression, treatment efficacy, etc. The terms "test subject" and "control subject" as used herein refer a mammals, preferably humans. The "control subject", according to the principles of the present invention refers to an individual that does not have cancer or any other chronic disease. The diagnosis, prognosis and/or monitoring of cancer comprises the diagnosis of a subject who is at risk of developing cancer, a subject who is suspected of having cancer, or a subject who was diagnosed with cancer using commonly available diagnostic tests (e.g. computed tomography (CT) scan). The present invention further provides the monitoring of cancer in patients having cancer. The term "monitoring" as used herein refers to the monitoring of disease progression or disease regression following treatment. Also encompassed by this term is the evaluation of treatment efficacy using the methods of the present invention.

According to the principles of the present invention the term "cancer" refers to a disorder in which a population of cells has become, in varying degrees, unresponsive to the control mechanisms that normally govern proliferation and differentiation. Cancer refers to various types of malignant neoplasms and tumors, including primary tumors, and tumor metastasis. In particular, the term "cancer" according to the principles of the present invention relates to breast, head and neck, colon, and/or prostate cancers. Each possibility represents a separate embodiment of the invention. Specific examples of these various cancer types include, but are not limited to, ductal carcinoma in situ (DCIS), lobular carcinoma in situ (LCIS), invasive ductal carcinoma (IDC), tubular carcinoma of the breast, medullary carcinoma of the breast, mucinous carcinoma of the breast, papillary carcinoma of the breast, cribriform carcinoma of the breast, invasive lobular carcinoma (ILC), Paget's disease of the nipple, inflammatory breast cancer, male breast cancer, oral cancer, laryngeal cancer, nasopharyngeal cancer, nasal cavity and paranasal sinus cancers, salivary gland cancer, thyroid cancer, adenocarcinoma, small cell carcinoma, squamous cell carcinoma, leiomyosarcoma, rhabdomyosarcoma, lymphoma, melanoma, neuroendocrine tumors, and sarcoma. Each possibility represents a separate embodiment of the invention. Encompassed by this term are different stages of the recited cancer types (i.e., Stages I, II, III, IV or V) as well as pre-cancerous conditions and metastasis to different sites.

The determination of the level of at least one volatile organic compounds is performed, according to the principles of the present invention, by the use of at least one technique including, but not limited to, Gas-Chromatography (GC), GC-lined Mass-Spectrometry (GC-MS), Proton Transfer Reaction Mass-Spectrometry (PTR-MS), Electronic nose device (E-nose), and Quartz Crystal Microbalance (QCM). Each possibility represents a separate embodiment of the invention.

Gas Chromatography (GC) linked to mass spectrometry (MS) is often used to determine the chemical identity and composition of breath VOCs (Miekisch et al. Clinica Chimica Acta, 2004, 347, 25-39). In this set-up, the GC utilizes a capillary column having characteristic dimensions (length, diameter, film thickness) as well as characteristic phase properties. The difference in the chemical properties of different molecules in a mixture allows the separation of the molecules as the sample travels through the column, wherein each molecule has a characteristic time (termed retention time) in which it passes through the column under set conditions. This allows the mass spectrometer to capture, ionize, accelerate, deflect, and detect the ionized molecules separately. The MS signal is obtained by ionization of the molecules or molecular fragments and measurement of their mass to charge ratio by comparing it to a reference collection.

Proton transfer reaction-mass spectrometry (PTR-MS) is reviewed in Lindinger et al., (Int. J. Mass Spectrom. Ion Process, 1998, 173, 191-241) and Lindinger et al., (Adv. Gas Phase Ion Chem., 2001, 4, 191-241). Briefly, PTR-MS measures VOCs that react with $H_3O^+$ ions that are added from an ion source. VOCs with a proton affinity that is larger than that of water (166.5 kcal×mol$^{-1}$) undergo a proton-transfer reaction with the $H_3O^+$ ions as follows: $H_3O^+$+ R→$RH^+$+$H_2O$. At the end of the drift tube reactor, a fraction of the ions is sampled by a quadrupole mass spectrometer, which measures the $H_3O^+$ and $RH^+$ ions. The ion signal at a certain mass is linearly dependent on the concentration of the precursor VOC in the sample air. In PTR-MS only the mass of VOCs is determined, causing some ambiguity in the identity of the VOCs. Thus, this technique does not allow a separate detection of different VOCs having the same mass. Further overlap of ion masses is caused by a limited degree of ion fragmentation and ion clustering in the drift tube.

Quartz Crystal Microbalance (QCM) is a piezoelectric-based device which can measure very small mass changes, mostly down to few nanograms. Briefly, QCM works by sending an electrical signal through a gold-plated quartz crystal, which causes vibrations in the crystal at a specific resonant frequency measured by the QCM. The resulted frequency shift can be translated to a change in mass on the QCM surface, mostly via using the Sauerbrey equation:

$$\Delta f = \frac{-2f_0^2}{A\sqrt{\rho_q \mu_q}} \Delta m$$

This equitation is used to correlate changes in the oscillation frequency of a piezoelectric crystal ($\Delta f$) with the mass deposited on it ($\Delta m$). Other parameters which affect the signals are the resonant frequency ($f_0$), the area between electrodes of the piezo-electric crystal (A), density ($\rho_q$) and shear modulus ($\mu_q$) of quartz.

Electronic nose devices perform odor detection through the use of an array of broadly cross-reactive sensors in conjunction with pattern recognition methods (see Rock et al, Chem. Rev., 2008, 108, 705-725). In contrast to the "lock-and-key" approach, each sensor in the electronic nose device is broadly responsive to a variety of odorants. In this architecture, each analyte produces a distinct fingerprint from the array of broadly cross-reactive sensors. This allows to considerably widen the variety of compounds to which a given matrix is sensitive, to increase the degree of component identification and, in specific cases, to perform an analysis of individual components in complex multi-component (bio) chemical media. Pattern recognition algorithms can then be used to obtain information on the identity, properties and concentration of the vapor exposed to the electronic nose device.

As used herein and in the appended claims the singular forms "a", "an," and "the" include plural references unless the content clearly dictates otherwise. Thus, for example, reference to "a sample" includes a plurality of such samples and so forth. It should be noted that the term "and" or the term "or" are generally employed in its sense including "and/or" unless the content clearly dictates otherwise.

The principles of the present invention are demonstrated by means of the following non-limiting examples.

EXAMPLES

Example 1

Test Population

Breath samples were taken from 46 volunteers aged 30-75, who had not ingested coffee or alcohol for at least 1 hour and 12 hours, respectively, after signed consent. The volunteers were divided as follows: 17 primary colon cancer patients, 15 primary breast cancer patients, and 14 primary prostate cancer patients. Additionally, 18 healthy individuals that matched the tested cancer patients in age and lifestyle were used as controls. All cancer patients were tested directly after being diagnosed by conventional clinical methods (e.g. computed tomography scan, colonoscopy, mammography etc.) and prior to chemotherapy and/or other cancer treatment. No breath collection was carried out in the 4 days following the biopsy. The clinical characteristics of the study population for cancer patients and healthy volunteers are listed in Table 1. Additional breath samples were taken from 59 healthy volunteers, aged 20-79, for studying the effect of various confounding factors. All experiments were approved by and performed according to the guidelines of the Technion's committee for supervision of human experiments (Haifa, Israel).

TABLE 1

Clinical characteristics of 46 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Cancer Stage | Additional data |
|---|---|---|---|---|---|---|---|---|
| Colon Cancer | | x | 1 | Y | | Tubolovillous adenoma | — | Pre-malignant |
| | x | x | 1 | N | N | Modified AC[(1)] | 1 | |
| | | x | 1 | N | Y | Rectum AC | 2 | |
| | x | | 1 | Y | | n/a | 2 | |
| | x | | 2 | N | N | n/a | 2 | |
| | x | | 1 | N | N | n/a | 2 | High blood pressure; Takes various medications |
| | x | | 1 | Y | | Rectum AC | 2 | High blood pressure; Takes various medications |
| | x | | 1 | N | N | n/a | 3 | Atrial fibrillation; Takes various medications |
| | x | x | 1 | N | Y | Rectum AC | 3 | Diabetes, high blood pressure; Takes various medications |
| | x | x | 1 | N | Y | Rectum AC | 3 | Hyperlipidemia, high blood pressure; Takes various medications |
| | x | x | 1 | N | N | Rectum AC | 3 | Diabetes, high blood pressure; Takes various medications |
| | x | | 1 | N | N | Rectum AC | 3 | |
| | x | | 1 | N | N | n/a | 4 | |
| | x | | 1 | Y | | Rectum AC | 4 | High blood pressure; Takes Normiten |
| | x | | 1 | Y | | Rectum AC | 4 | |
| | x | x | 1 | Y | | NEC[(2)] | 4 | |
| Breast Cancer | x | | 1 | N | N | n/a | 1 | Heart disease, High blood pressure, Osteoporosis; Takes various medications |
| | x | | 1 | N | N | n/a | 1 | Thrombocytopenia; Takes various medications |
| | | x | 1 | N | N | IDC[(3)] | 1 | Gastritis, high blood pressure; Takes various medications |
| | x | | 1 | N | N | IDC | 2 | High blood pressure, Hyperlipidemia; Takes Cilaril Plus and Simovil |
| | | x | 1 | N | N | n/a | 3 | |
| | | x | 1 | N | N | n/a | 3 | Epilepsy; Takes Douplephat, Lamictal and Clonex |
| | x | | 1 | N | N | n/a | n/a | High blood pressure, Diabetes; Takes various medications |
| | x | x | 1 | N | N | IDC | n/a | |
| | x | | 1 | N | N | IDC | n/a | |
| | x | | 1 | N | Y | IDC | n/a | Hypo activity of |

TABLE 1-continued

Clinical characteristics of 46 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Cancer Stage | Additional data |
|---|---|---|---|---|---|---|---|---|
| | | | | | | | | the thyroid glands; Takes Eltroxin and vitamins |
| | | x | 1 | N | N | n/a | n/a | |
| | x | | 1 | N | N | n/a | n/a | |
| | x | | 1 | Y | | n/a | n/a | Several medical conditions; Takes various medications |
| | x | | 1 | N | N | n/a | n/a | Diabetes |
| | x | | 1 | n/a | n/a | n/a | n/a | |
| Prostate Cancer | x | | 1 | N | N | AC | 1 | |
| | x | | 1 | N | N | AC | 1 | Glaucoma; Takes various medications |
| | x | | 1 | N | N | AC | 1 | Diabetes; Takes various medications |
| | | x | 1 | N | N | n/a | 1 | High blood pressure; Takes Enaladex |
| | | x | 1 | N | N | n/a | 1 | Diabetes, Bypass; Takes various medications |
| | x | | 1 | N | N | AC | 1 | High blood pressure; Takes various medications |
| | x | | 1 | N | N | AC | 1 | Diabetes, high blood pressure and Hyperlipidemia; Takes various medications |
| | x | | 1 | N | Y | AC | 1 | Cardiac arrythmia; Takes various medications |
| | x | | 1 | N | Y | AC | 1 | |
| | x | x | 1 | N | N | AC | 1C | Several health conditions; Takes various medications |
| | x | | 1 | N | N | AC | 2 | Several health conditions; Takes various medications |
| | x | x | 1 | N | N | AC | 2 | Diabetes, Brain stroke two year prior to breath test; Takes various medications |
| | | x | 1 | Y | | n/a | 2 | Back problems; Takes Casodex |
| | | x | 1 | Y | | AC | 4 | High blood pressure; Takes Enaladex and Clexane |
| Healthy Control | x | x | 4 | N | N | | | |
| | x | | 5 | N | N | | | |
| | | x | 2 | N | N | | | |
| | | x | 1 | Y | | | | |
| | x | x | 1 | N | N | | | Sub activity of the thyroids glands; Takes Latroxin |
| | x | x | 1 | N | N | | | High blood pressure |
| | | x | 1 | N | N | | | High blood pressure; Takes blood pressure |

TABLE 1-continued

Clinical characteristics of 46 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Cancer Stage | Additional data |
|---|---|---|---|---|---|---|---|---|
| | x | | 1 | N | N | | | regulating medications Takes Eltroxin |
| | x | x | 1 | Y | | | | Diabetes |
| | x | | 1 | n/a | n/a | | | |

[1]AC = Adenocarcinoma
[2]Nero-Endocrin Carcinoma
[3]IDC = Invasive Duct Carcinoma

Example 2

Breath Collection

Exhaled breath was collected in a controlled manner from the test population of example 1. Inhaled air was cleared of ambient contaminants by repeatedly inhaling to total lung capacity for 5 minutes through a mouthpiece (purchased from Eco Medics) that contained a filter cartridge on the aspiratory port, thus removing more than 99.99% of the exogenous VOCs from the air during inspiration. Immediately after lung washout, the subjects exhaled through a separate exhalation port of the mouthpiece against 10-15 cm $H_2O$ pressure to ensure closure of the vellum to exclude nasal entrainment of gas. Exhaled breath contained a mixture of alveolar air and respiratory dead space air. Subjects exhaled into the breath collector which automatically filled the dead space air into a separate bag and the alveolar breath into a 750 ml Mylar sampling bag (polyvinyl fluoride, purchased from Eco Medics) in a single-step process. The Mylar bags were re-used and thoroughly cleaned prior to each use with flowing $N_{2(g)}$ (99.999% purity) for 5-8 minutes (GC-MS in conjugation with pre-concentration techniques showed that this purification process eliminates >99% of the contaminants and/or VOCs from the Mylar bags). At least two bags were collected from each individual for subsequent analysis. All bags were analyzed within two days from the time of breath collection to assure accuracy of the results.

Example 3

GC-MS Measurements

Breath samples were analyzed with gas chromatography-mass spectroscopy (GC-MS; GC-6890N; MS-5975; Agilent Technologies Ltd.) combined with solid phase microextraction (SPME). The SPME technique is used for pre-concentrating VOCs from the breath samples. A manual SPME holder with an extraction fiber coated with: 1) Polydimethylsiloxane (PDMS), 2) Polydimethylsiloxane-Divinylbenzene (PDMS/DVB), or 3) Polydimethylsiloxane-Carboxen (PDMS/Carboxen) (purchased from Sigma-Aldrich) was inserted into the Mylar bag for 20-30 minutes. The SPME holder was then delivered to the GC-MS. Between 500 and 1,000 $cm^3$ of each breath sample was concentrated via the SPME method during the extraction period of 2 hours, and delivered to the GC-MS using a manual SPME holder. The extracted fiber in the manual SPME holder was inserted into a GC injector which operated using the splitless model. The oven temperature profile was: 60° C., 2 min, 8° C./min to 100° C., 15° C./min to 120° C., 8° C./min to 180° C., 15° C./min to 200° C., 8° C./min to 225° C. Capillary column H5-5MS 5% Phenyl Methyl Siloxane (30 m length, 0.25 mm i.d., 0.25 μm thickness) was used. The column pressure was set to 8.22 psi, and initial flow was 1.0 mL/min. Finally, the molecular structures of the VOCs were determined via the Standart Modular Set.

Example 4

Breath Analysis

Figure 1B:
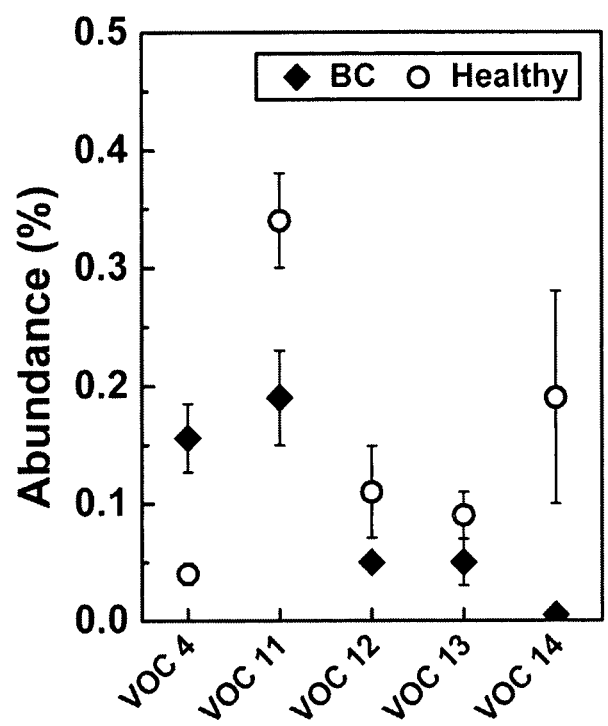
FIG. 1B. The abundance of 5 VOCs detected in breath samples of breast cancer patients (BC) and control individuals (healthy). VOC 4=3,3-dimethyl pentane (m/z=43); VOC 11=2-amino-5-isopropyl-8-methyl-1-azulenecarbonitrile (m/z=224); VOC 12=5-(2-methylpropyl)nonane (m/z=57); VOC 13=2,3,4-trimethyl decane (m/z=43); and VOC 14=6-ethyl-3-octyl ester 2-trifluoromethyl benzoic acid (m/z=173).
Figure 1C:
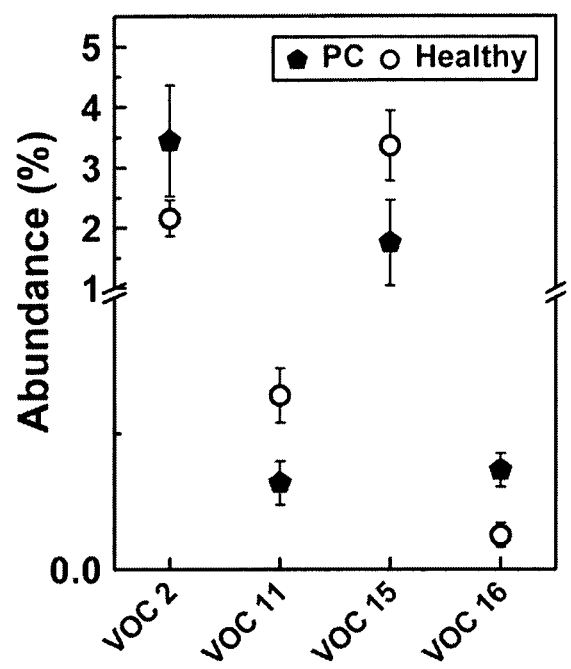
FIG. 1C. The abundance of 4 VOCs detected in breath samples of prostate cancer patients (PC) and control individuals (healthy). VOC 2=toluene (m/z=91); VOC 11=2-amino-5-isopropyl-8-methyl-1-azulenecarbonitrile (m/z=224); VOC 15=p-xylene (m/z=91); and VOC 16=2,2-dimethyl decane (m/z=57).
Figure 2A:
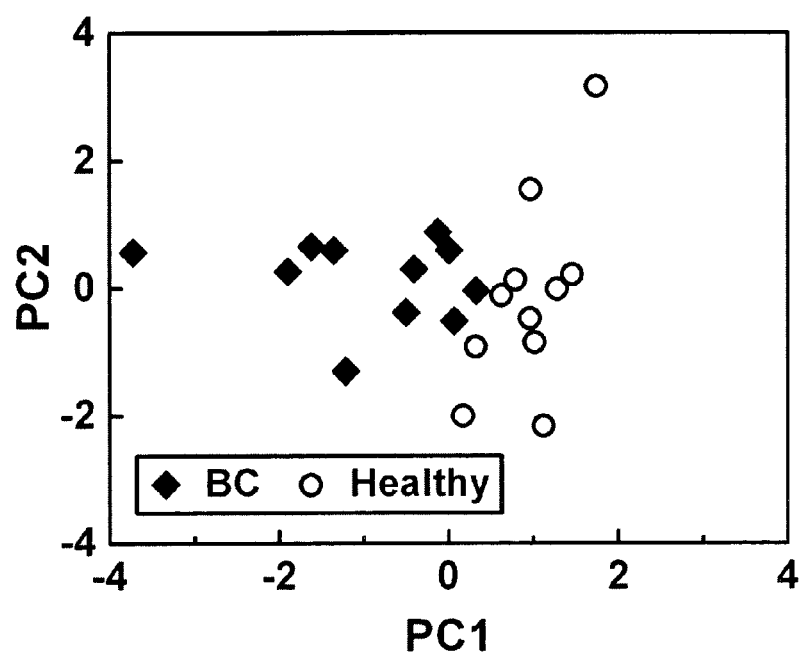
FIG. 2A. A Principle Component Analysis (PCA) plot of the GC-MS/SPME analysis of breast cancer patients and control individuals using 5 VOCs. The abundances of the VOCs used for the analysis are shown in FIG. 1B. Each point represents one subject.
Figure 2B:
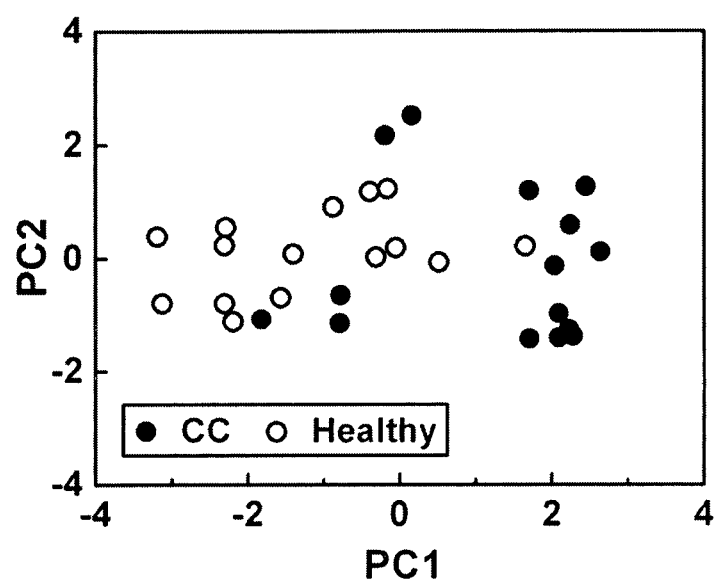
FIG. 2B. A Principle Component Analysis (PCA) plot of the GC-MS/SPME analysis of colon cancer patients and control individuals using 6 VOCs. The abundances of the VOCs used for the analysis are shown in FIG. 1A. Each point represents one subject.
Figure 2C:
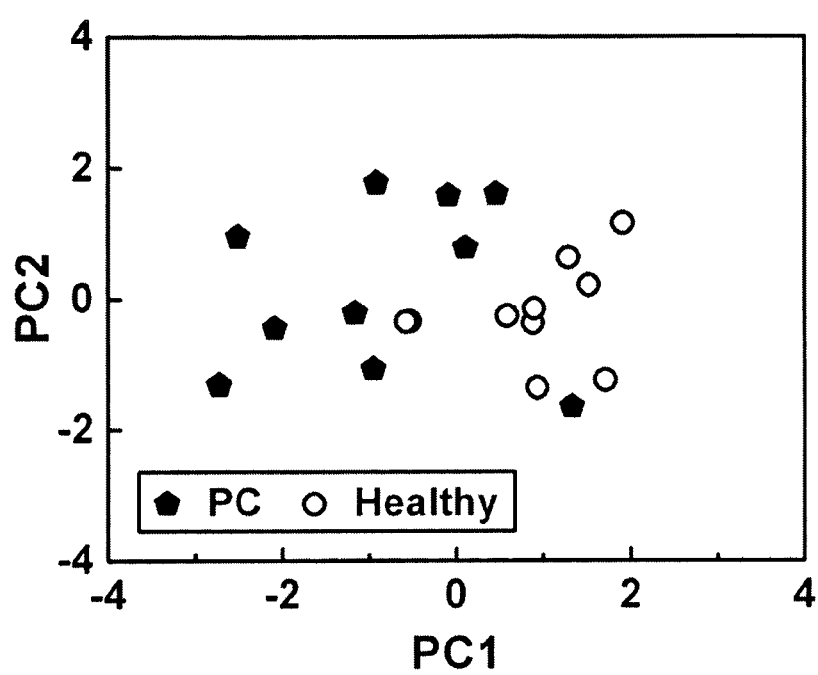
FIG. 2C. A Principle Component Analysis (PCA) plot of the GC-MS/SPME analysis of prostate cancer patients and control individuals using 4 VOCs. The abundances of the VOCs used for the analysis are shown in FIG. 1C. Each point represents one subject.

The VOCs which were found in more than 80% of the control (healthy) and test (cancer) samples, as well as their abundance with experimental error, were identified by the Automated Mass Spectral Deconvolution and Identification System (AMDIS) software. This was done separately for each of the cancer types (colon, breast, and prostate) vs. control samples and also for all cancer types vs. control samples in a single plot. 39, 54 and 36 VOCs were identified in more than 80% of tested samples (colon, breast and prostate cancers, respectively) and control samples. In order to establish characteristic smell prints of the different types of cancer, different VOCs for each cancer type were chosen such that no overlap in abundance (cf. error bars) between controls and cancer patients was found. In samples from colon cancer patients 6 VOCs were chosen (FIG. 1A), in samples from breast cancer patients 5 VOCs were chosen (FIG. 1B), and in samples from prostate cancer patients 4 VOCs were chosen (FIG. 1C) (see also Peng et al., British Journal of Cancer, 2010, 103(4), 542-551, published after the priority document U.S. 61/292,872). Smell prints from the representative compounds were determined using standard principal component and cluster analysis. FIG. 2A shows a good discrimination between samples of breast cancer patients and control individuals. FIGS. 2B and 2C show reasonable separation between samples of colon cancer and prostate cancer, respectively, and control individuals.

Example 5

Absolute Values of VOCs in Breath Samples of Cancer Patients

The absolute values of the VOCs which are present in breath samples of cancer patients (breast, head and neck, prostate and colon) and control individuals were determined as follows: 14 compounds were chosen as standards for GC based on the GC-MS results of the clinical study: (1) Nonanal; (2) 2-Butanone; (3) Undecane; (4) Toluene; (5) Tetrachloroethylene; (6) Pyrrolidine; (7) Decane; (8) Octane; (9) P-xylene; (10) Ethylbenzene; (11) Heptane; (12) Acetic Acid; (13) Benzene and (14) Isoprene.

The standard samples were prepared using either a gas simulator system or a manual method depending on the boiling point of each compound. At least three different concentrations were prepared for each standard. The standards were collected in 750 ml Mylar sampling bags, which were thoroughly cleaned before each use with zero air (air devoid of VOCs) for 15 minutes followed by flowing nitrogen for 1-2 min.

The standards were pre-concentrated using manual SPME fibers, similarly to the process described in example 3 hereinabove. Three fibers with different coatings were used: (i) polydimethylsiloxane-divinylbenzene (PDMS/DVB; referred to as "blue fiber"), (ii) polydimethylsiloxane (PDMS; referred to as "red fiber"), or (iii) polydimethylsiloxane-carboxen (PDMS/Carboxen; referred to as "black fiber"). Following a period of 2 hours of extraction, the fibers were transferred to the GC-MS using a manual SPME holder. The oven temperature profile was: 60° C., 2 min, 8° C. $min^{-1}$ to 100° C., 15° C. $min^{-1}$ to 120° C., 8° C. $min^{-1}$ to 180° C., 15° C. $min^{-1}$ to 200° C., 8° C. $min^{-1}$ to 225° C. Capillary column H5-5MS 5% phenyl methyl siloxane (30 m length; 0.25 mm i.d., 0.25 mm thickness) was used (Agilent Technologies). The column pressure was set to 8.22 psi and initial flow was 1.0 ml $min^{-1}$. At the end of the extraction process the bag was connected to a Photoionization detector (PID) in order to measure the concentration in the bag.

For each compound, a calibration curve of the integrated signal (area under the peak; y-axis) calculated using AMDIS (Automatic Mass Spectral Database) software vs. the multiplication product between the concentration measured by the PID using the matching correction factor and the abundance of the compound (x-axis) was prepared.

The breath samples of the patients were measured and analyzed using the same protocol as the standards. For a specific compound, the integrated signal was calculated for all patient samples in which the compound appeared. The concentration of the compound was calculated by dividing the mean of the integrated signal values by the slope of the calibration curve.

The absolute values of selected VOCs which are present in breath samples of breast cancer patients are listed in table 2. The absolute values of selected VOCs which are present in breath samples of head and neck cancer patients are listed in table 3. The absolute values of selected VOCs which are present in breath samples of prostate cancer patients are listed in table 4. The absolute values of selected VOCs which are present in breath samples of colon cancer patients are listed in table 5. The absolute values of the selected VOCs which are present in breath samples of control individuals are listed in table 6.

TABLE 2

Absolute values of selected VOCs in breath samples of breast cancer patients

| VOC in breath samples of breast cancer patients | RT | Blue Fiber (ppb) | Red Fiber (ppb) | Black Fiber (ppb) |
|---|---|---|---|---|
| Pentane, 3,3-dimethyl- | 8.06 (isomer) | 18.1 ± 1.8 | | |
| Pentane, 3,3-dimethyl- | 1.97 (not isomer) | 27.6 ± 5.9 | | |
| Nonane, 5-(2-methylpropyl)- | 11.6 | 0.64 ± 0.18 | | |
| 2-Amino-5-isopropyl-8-methyl-1-azulenecarbonitrile | 18.2 | 402.8 ± 214.1 | | |
| Decane, 2,3,4-trimethyl- | 8.06 | 0.58 ± 0.26 | | |
| 2-Trifluoromethylbenzoic acid, 6-ethyl-3-octyl ester | | — | | |
| 2,3,4,6-Tetramethoxystyrene | 18.2 | | 0.65 ± 0.58 | |
| Phenol, 2,4,6-tris(1-methylethyl)- | | — | | |
| Nonane, 2,2,4,4,6,8,8-heptamethyl- | 11.9 | | 1.04 ± 0.20 | |
| Ethyl benzene | 4.19 | | 66.9 ± 56.6 | |
| 2,2,4,4,5,5,7,7-Octamethyloctane | 11.9 | | 1.11 ± 0.11 | |
| 1,3-Butadiene, 2-methyl- | 1.5 | | | 9.23 ± 8.45 |
| 1,3,5-Cycloheptatriene | 2.8 | | | 48.0 ± 32.6 |
| Hydroxymethyl 2-hydroxy-2-methylpropionate | | | | — |
| Ethanol, 2-methoxy-, acetate | 1.506 | | | 108.3 ± 97 |
| Hexane, 2-methyl- | 2.01 | | | 59.3 ± 38 |

TABLE 3

Absolute values of selected VOCs in breath samples of head and neck cancer patients

| VOC in breath samples of head and neck cancer patients | RT | Blue Fiber (ppb) | Red Fiber (ppb) | Black Fiber (ppb) |
|---|---|---|---|---|
| 2-Acetylmethylamino-4,5,6,7-tetrahydrobenzothiazol-7-one | 18.18 | 64.8 ± 76.3 | | |
| Butylated Hydroxytoluene | 14.79 | 32.0 ± 63.8 | | |

TABLE 3-continued

Absolute values of selected VOCs in breath samples of head and neck cancer patients

| VOC in breath samples of head and neck cancer patients | RT | Blue Fiber (ppb) | Red Fiber (ppb) | Black Fiber (ppb) |
|---|---|---|---|---|
| Nonane, 2,2,4,4,6,8,8-heptamethyl- | 11.94 | 3.27 ± 3.27 | 0.52 ± 0.41 | |
| Benzoic acid, 4-(4-propylcyclohexyl)-, 4'-cyano [1,1'-biphenyl]-4-yl ester | | | — | |
| Carbonic dihydrazide | | | — | |
| Benzene, 1-methyl-3-(1-methylethyl)- | 7.19 | | 19.39 ± 14.16 | |
| Phenol, 4,6-di(1,1-dimethylethyl)-2-methyl- | | | — | |
| 1-propanol | 1.61 | | | 260.9 ± 146 |
| 1,3-Butadiene, 2-methyl- (Isoprene) | 1.53 | | | 5.81 ± 3.68 |
| Bicyclo[2.2.1]heptane, 2,2,3-trimethyl- | | | | — |
| 1,3-Pentadiene, (E)- (as Isoprene) | 1.53 | | | 4.30 ± 2.80 |

TABLE 4

Absolute values of selected VOCs in breath samples of prostate cancer patients

| VOC in breath samples of prostate cancer patients | RT | Blue Fiber (ppb) | Red Fiber (ppb) | Black Fiber (ppb) |
|---|---|---|---|---|
| p-Xylene | 4.19 | 1.52 ± 0.69 | | |
| toluene | 2.86 | 82.9 ± 54.8 | | |
| 2-Amino-5-isopropyl-8-methyl-1-azulenecarbonitrile | 18.24 | 338.8 ± 155.8 | | |
| Decane, 2,2-dimethyl- | 6.5 | 2.29 ± 1.17 | | |
| Carbonic dihydrazide | | | — | |
| Phenol, 4,6-di(1,1-dimethylethyl)-2-methyl- | | | — | |
| 2,2,4,4,5,5,7,7-Octamethyloctane | 11.94 | | 4.01 | |
| Benzene, 1,1'-(1,3,3-trimethyl-1-propene-1,3-diyl)bis- | 17.54 | | 4.22 ± 2.21 | |
| 1,3-Butadiene, 2-methyl- | 1.53 | | | 9.8 ± 5.22 |
| α-Phellandrene | | | | — |
| Butylated Hydroxytoluene | 14.78 | | | 44.7 ± 42.2 |
| Diazene, dimethyl- | | | | — |
| Benzene, 1-ethyl-3,5-dimethyl- | 9.13 | | | 6.29 |

TABLE 5

Absolute values of selected VOCs in breath samples of colon cancer patients

| VOC in breath samples of colon cancer patients | RT | Blue Fiber (ppb) | Red Fiber (ppb) | Black Fiber (ppb) |
|---|---|---|---|---|
| Benzene, 1-methyl-3-(1-methylethyl)- | 7.19 | 29.8 ± 21.9 | | |
| Benzene, 1,1'-(1-butenylidene)bis- | 17.3 | 1.50 ± 0.67 | | |
| Nonane, 1-iodo- | 7.62 | 0.89 ± 0.64 | | |
| Acetic acid, [(1,1-dimethylethyl)thio]- | 3.14 | 28.2 ± 16.3 | | 20.1 ± 12.6 |
| 2-Amino-5-isopropyl-8-methyl-1-azulenecarbonitrile | 18.24 | 310.8 ± 167.1 | | |
| 1,3,5-Cycloheptatriene | 2.87 | 40.26 ± 14.26 | | |
| Hexane, 3,3-dimethyl- | 7.36 | | 6.59 ± 2.80 | |

TABLE 5-continued

Absolute values of selected VOCs in breath samples of colon cancer patients

| VOC in breath samples of colon cancer patients | RT | Blue Fiber (ppb) | Red Fiber (ppb) | Black Fiber (ppb) |
|---|---|---|---|---|
| Benzene, 1-ethyl-2,4-dimethyl- | 7.201 | | 20.50 ± 12.24 | |
| Phenol, 2,4,6-tris(1-methylethyl)- | | | — | |
| Benzene, 1,1'-(3-methyl-1-propene-1,3-diyl)bis- | 17.15 | | 15.53 ± 5.49 | |
| Phenol, 2,6-bis(1,1-dimethylethyl)-4-methyl-, methylcarbamate | | | | |
| Trans-1,4-diethylcyclohexane | | | — | |
| 1,3-Butadiene, 2-methyl- | 1.53 | | | 17.05 ± 12.22 |
| Ammonium acetate | | | | |
| Bicyclo[2.2.1]heptane, 2,2,3-trimethyl-, endo- | | | | — |
| Diazene, dimethyl- | | | | — |

TABLE 6

Absolute values of selected VOCs in breath samples of control individuals

| VOC in breath samples of control individuals | RT | Blue Fiber (ppb) | Red Fiber (ppb) | Black Fiber (ppb) |
|---|---|---|---|---|
| 1,3,5-Cycloheptatriene | 2.8 | 30.13 ± 14.45 | | 76.4 ± 50.8 |
| 1,3-Butadiene, 2-methyl- (Isoprene) | 1.53 | | | 18.81 ± 12.92 |
| 1,3-Pentadiene, (E)- (as Isoprene) | 1.53 | | | 20.79 ± 14.04 |
| 1-propanol | 1.61 | | | 204.8 ± 157.4 |
| 2,2,4,4,5,5,7,7-Octamethyloctane | 11.9 | | 2.50 ± 1.73 | |
| 2,3,4,6-Tetramethoxystyrene | 18.2 | | 3.59 ± 3.69 | |
| 2-Acetylmethylamino-4,5,6,7-tetrahydrobenzothiazol-7-one | 18.18 | 101.6 ± 21.7 | | |
| 2-Amino-5-isopropyl-8-methyl-1-azulenecarbonitrile | 18.24 | 338.9 ± 191.8 | | |
| Acetic acid, [(1,1-dimethylethyl)thio]- | 3.14 | 27.05 ± 11.97 | | 18.73 ± 7.80 |
| Benzene, 1,1'-(1,3,3-trimethyl-1-propene-1,3-diyl)bis- | 17.54 | | 12.73 ± 7.57 | |
| Benzene, 1,1'-(1-butenylidene)bis- | 17.3 | 2.50 ± 1.21 | | |
| Benzene, 1,1'-(3-methyl-1-propene-1,3-diyl)bis- | 17.15 | | 16.58 ± 8.33 | |
| Benzene, 1-ethyl-2,4-dimethyl- | 7.201 | | 6.98 ± 4.09 | |
| Benzene, l-ethyl-3,5-dimethyl- | 9.13 | | | — |
| Benzene, 1-methyl-3-(1-methylethyl)- | 7.19 | | 14.08 ± 5.74 | |
| Benzene, 1-methyl-4-(1-methylethyl)- | 7.19 | 45.55 ± 23.52 | | |
| Butylated Hydroxytoluene | 14.79 | 23.20 ± 43.57 | | 166.0 ± 87.5 |
| Decane, 2,2-dimethyl- | 6.5 | 0.48 ± 0.22 | | |
| Decane, 2,3,4-trimethyl- | 8.06 | 0.37 ± 0.26 | | |
| Dodecane | 7.74 | 3.30 ± 2.06 | | |
| Ethanol, 2-methoxy-, acetate | 1.506 | | | 8356.9 ± 899.2 |
| Ethyl alcohol | 1.447 | | | 1282.7 ± 835.2 |
| Ethyl benzene | 4.19 | | 74.3 ± 43.1 | |
| Hexane, 2,3,4-trimethyl- | 3.52 | 81.8 ± 38.8 | | |
| Hexane, 2-methyl- | 2.01 | | | 241.5 ± 180.4 |
| Hexane, 3,3-dimethyl- | 7.36 | | 6.91 | |
| Nonane, 1-iodo- | 7.62 | — | | |

TABLE 6-continued

Absolute values of selected VOCs in breath samples of control individuals

| VOC in breath samples of control individuals | RT | Blue Fiber (ppb) | Red Fiber (ppb) | Black Fiber (ppb) |
|---|---|---|---|---|
| Nonane, 2,2,4,4,6,8,8-heptamethyl- | 11.94 | 1.57 ± 1.31 | 2.36 ± 1.60 | |
| Nonane, 5-(2-methylpropyl)- | 11.6 | 0.55 ± 0.23 | | |
| o-Xylene | 4.18 | | | 46.3 ± 28.3 |
| Pentane, 3,3-dimethyl- | 1.96 | 6.89 ± 4.29 | | |
| p-Xylene | 4.19 | 64.4 ± 23.6 | | |
| styrene | 4.68 | | | 41.7 ± 25.9 |
| Toluene | 2.8 | 54.2 ± 28.9 | | |

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A method of treating breast cancer in a human comprising the steps of:
  a) collecting a test breath sample from the human subject, wherein the human subject performs lung washout for at least about 5 minutes and exhales into a breath collector;
  b) extracting volatile organic compounds (VOCs) from the breath test sample, wherein the VOCs are absorbed in a solid support, adsorbed on a solid support or a combination thereof;
  c) determining the level of each VOC from a signature set of VOCs indicative of breast cancer extracted from the test sample, wherein the signature set comprises
  2-amino-5-isopropyl-8-methyl-1-azulenecarbonitrile;
  6-ethyl-3-octyl ester-2-trifluoromethylbenzoic acid;
  3,3-dimethyl-pentane;
  5-(2-methylpropyl)-nonane; and
  2,3,4-trimethyl-decane, and
  wherein the step of determining the level of said VOCs comprises the use of Gas-Chromatography-Mass Spectrometry (GC-MS);
  d) comparing the level of each of said VOCs from the test sample with the level of said VOCs in a control sample, whereby a statistically significant decrease with a p-value of less than 0.05 in the levels of
  2-amino-5-isopropyl-8-methyl-1-azulenecarbonitrile;
  6-ethyl-3-octyl ester-2-trifluoromethylbenzoic acid;
  5-(2-methylpropyl)-nonane; and
  2,3,4-trimethyl-decane and
  a statistically significant increase with a p-value of less than 0.05 in the level of 3,3-dimethyl-pentane in the test sample as compared to the levels of said VOCs in the control sample is indicative of the presence of breast cancer in the human subject, wherein said control sample is obtained from a subject not having cancer; and
  administering a specific therapeutically effective treatment for breast cancer to the human subject having the statistically significant levels identified in step (d) that indicates the presence of breast cancer in said human subject, wherein said therapeutically effective treatment is chemotherapy.

2. The method of claim 1, wherein the human subject is selected from a human subject who is at risk of developing breast cancer, a human subject who is suspected of having breast cancer, and a human subject who is afflicted with breast cancer.

3. The method of claim 1, comprising determining the level of at least one additional VOCs selected from the group consisting of
  2,3,4,6-tetramethoxystyrene;
  2,4,6-tris(1-methylethyl)-phenol;
  1,3,5-cycloheptatriene;
  2-methoxy-acetate ethanol;
  2-methyl-1,3-butadiene;
  2,2,4,4,6,8,8-heptamethyl-nonane;
  ethyl benzene;
  2,2,4,4,5,5,7,7-octamethyloctane;
  hydroxymethyl 2-hydroxy-2-methylpropionate; and
  2-methyl-hexanehexane.

4. The method of claim 1, wherein the levels of VOCs from the signature set form a pattern which is significantly different from the pattern of said VOCs in the control sample.

5. The method according to claim 4, wherein the pattern is analyzed with a pattern recognition analyzer, wherein the pattern recognition analyzer comprises at least one algorithm selected from the group consisting of principal component analysis (PCA), artificial neural network algorithms, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

6. The method according to claim 1, wherein GC-MS is combined with solid phase microextraction (SPME).

7. The method according to claim 6, wherein the solid phase microextraction comprises the use of extraction fibers coated with at least one polymer selected from the group consisting of polydimethylsiloxane, polydimethylsiloxane-divinylbenzene and polydimethylsiloxane-carboxen.

* * * * *